United States Patent [19]

Schluter et al.

[11] Patent Number: 4,968,302
[45] Date of Patent: Nov. 6, 1990

[54] AUTOMATIC INJECTION DEVICE, INCLUDING AN AMPOULE OR A CARTRIDGE FOR AN INJECTION DEVICE

[75] Inventors: Eberhardt Schluter, Elfenbeinweg 13, Hamburg 65; Albert Scheller, Gaggenau; Rolf Sprenger, Gaggenau/Winkel, all of Fed. Rep. of Germany

[73] Assignee: Eberhardt Schluter, Hamburg, Fed. Rep. of Germany

[21] Appl. No.: 167,473

[22] PCT Filed: Jun. 24, 1987

[86] PCT No.: PCT/EP87/00332
§ 371 Date: Apr. 26, 1988
§ 102(e) Date: Apr. 26, 1988

[87] PCT Pub. No.: WO88/00066
PCT Pub. Date: Jan. 14, 1988

[30] Foreign Application Priority Data

Jul. 1, 1986 [DE] Fed. Rep. of Germany ....... 3622399

[51] Int. Cl.⁵ .............................................. A61M 57/00
[52] U.S. Cl. ..................... 604/135; 604/87; 604/138; 604/139; 604/416
[58] Field of Search ............... 604/135, 136, 138, 139, 604/143, 144, 157, 156, 232, 87-90, 201-205, 416, 195-196

[56] References Cited

U.S. PATENT DOCUMENTS

| | | | |
|---|---|---|---|
| 2,460,039 | 1/1949 | Scherer et al. | 604/201 X |
| 2,626,604 | 1/1953 | Nadeau | 604/156 |
| 2,701,566 | 2/1955 | Krug | 604/156 |
| 2,704,072 | 3/1955 | Sarnoff | 604/138 |
| 2,769,443 | 11/1956 | Dunmire | 604/195 |
| 2,832,339 | 4/1958 | Sarnoff et al. | 604/138 |
| 2,866,458 | 12/1958 | Hein, Jr. | 604/138 |
| 3,066,670 | 12/1962 | Stauffer | 604/139 |
| 3,426,448 | 2/1969 | Sarnoff | 604/135 |
| 3,739,947 | 6/1973 | Baumann et al. | 604/87 X |
| 3,797,489 | 3/1974 | Sarnoff | 604/136 |
| 4,178,928 | 12/1979 | Tischlinger | 604/139 |
| 4,202,314 | 5/1980 | Smirnov et al. | 604/138 |
| 4,214,584 | 6/1980 | Smirnov et al. | 604/157 |
| 4,306,554 | 12/1981 | Schwartz et al. | 604/87 |
| 4,316,463 | 2/1982 | Schmitz et al. | 604/157 |
| 4,565,543 | 1/1986 | Bekkering et al. | 604/135 |
| 4,723,937 | 2/1988 | Sarnoff et al. | 604/136 |

*Primary Examiner*—C. Fred Rosenbaum
*Assistant Examiner*—C. Maglione
*Attorney, Agent, or Firm*—Fay, Sharpe, Beall, Fagan, Minnich & McKee

[57] ABSTRACT

Automatic injection device, as well as ampoule or cartridge for the same. In order to obtain a high speed discharge of an ampoule-hypodermic needle, as well as to ensure an operationally reliable, low weight, robust small apparatus or ampoule at long storability, sterility and re-usability of components for a plurality of injection substances, the needle body (30) of the cannulahypodermic needle (3) is constructed over part of its extension as a needle bearing (31) guided in sliding fit on the inner wall (21) of the cartridge (2). Particularly with a view to administering separate injection substances, it is provided for a cartridge or ampoule with needle and lifting element, that within the ampoule there is arranged a receptacle forming a gas volume, which receptacle can be destroyed easily by initiating the lifting movement and which is resistant to the injection fluid surrounding it.

42 Claims, 4 Drawing Sheets

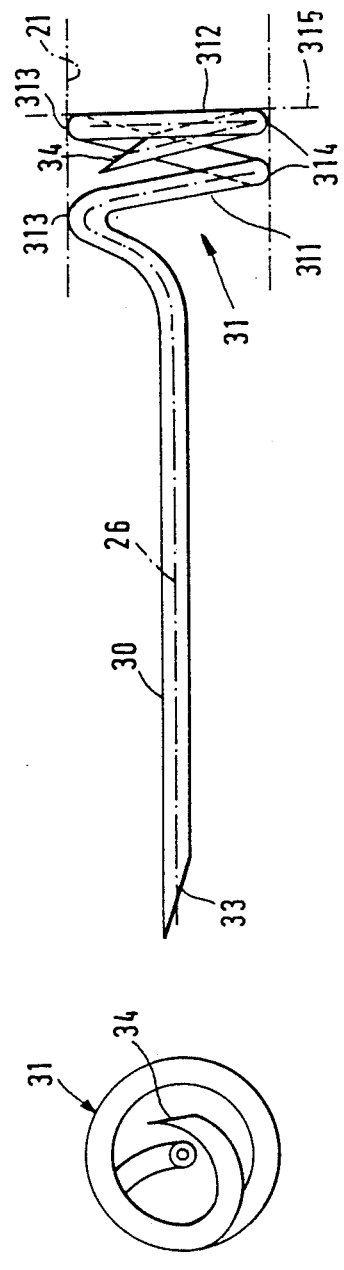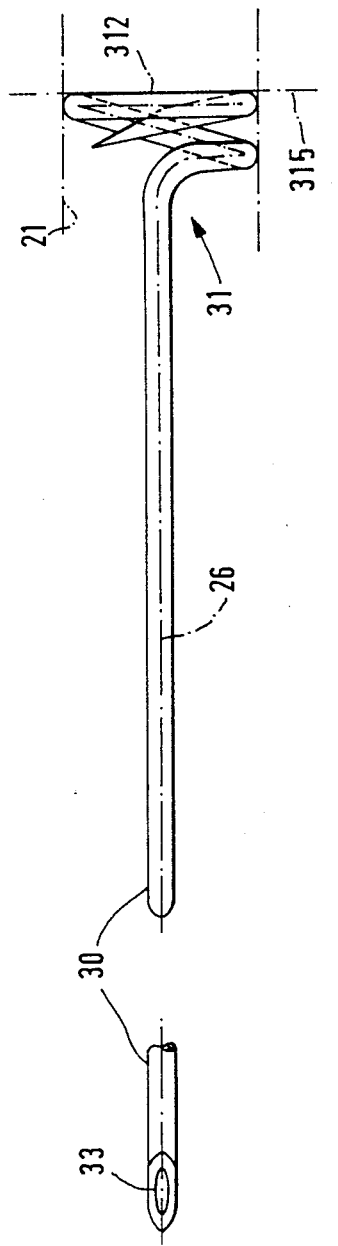

AUTOMATIC INJECTION DEVICE, INCLUDING AN AMPOULE OR A CARTRIDGE FOR AN INJECTION DEVICE

The invention relates to an automatic injection or hypodermic device, including a cartridge or ampoule, which is mounted in a casing, receives an injection substance, has a lifting element, surrounds an injection or hypodermic needle comprising an elongated needle body and a cannula or tubule. The needle being movable by the lifting element and has cannula inlet opening for the injection substance in the region of its drive-side end A seal arranged on the side of the needle point permits the passage of the needle shaft. An injection pressure device mounted on the casing applies a force to the lifting element. A release mechanism puts the pressure device into operation; and includes a safety device for blocking the release mechanism. A cartridge or ampoule for use in injection devices, particularly in an automatic hypodermic syringe, has an injection substance in the cartridge or ampoule that is ejectable, as a result of the lifting movement of a lifting element, such as in particular a plunger or bolt, through a cannula of an injection needle mounted on the cartridge or ampoule.

An automatic self-injection syringe gives unskilled persons an opportunity to make a subcutaneous or intramuscular self injection. This has particular significance in connection with the injection of atropine sulphate as a nerve gas preventative. In addition, atropine is injected as an effective antidote in the case of insecticide poisonings. Atropine is also injected, e.g. in the case of spasms and colics in the gastrointestinal tract, in the gall bladder or the discharging urinary passages, of bladder tenesmus, of hypersecretion of the stomach, of gastric and duodenal ulcers, bronchial asthma and in higher doses and over longer periods in the case of Parkinsonism. An automatic injection device can, in general, be used for the application of a large number of injection substances in human or veterinary medicine. Possibilities of use also exist in the technical field. Thus, in particular dangerous or toxic substances can be introduced into soft materials, mention being, for example, made of the preservation of soft wood or similar treatments. The injection substances can be constituted by liquids, gases or pressure-liquifiable substances.

Essential demands made on an automatic injection device consist in sterility, durability and stability even over long storage periods, in very rapid and reliable penetration of tissue parts having pain receptors by the needle, if necessary also after piercing articles of clothing, in low weight and compact construction, as well as in simple and operationally reliable handling.

In a known injection device of this type, a needle is mounted in an ampoule by localizing a needle base on a lifting plunger, as well as on the discharge side in a needle guide and a rubber plunger. A helical compression spring engages the ampoule sleeve for advancing the lifting plunger. In the case of such a construction, the guidance and mobility of the needle are impaired due to the decelerating effect of the relatively long rubber bearing and this can lead to a moment of force having an unfavourable action on the alignment and movement of the needle. A cannula opening provided on the needle base, i.e. a weakened needle portion at this point, can lead to a deformation or even breakage of the needle. To ensure that an adequate force is applied to the lifting plunger or for driving the needle, a relatively high force is required, which has to be imposed by the relatively long helical compression spring having a relatively large coil diameter, the spring following the plunger in an inner sleeve mounting both it and the ampoule, and engaging in the latter during operation. The ampoule body is made from stainless steel in order to withstand the force stressing. Due to catalytic effects and chemical and/or galvanic reactions of the metal with the injection substance, the stability and effectiveness thereof is reduced. Stainless steel is not inert for many injection substances, so that it cannot be used as ampoule material. The pressure device and, therefore, the complete device have relatively large dimensions, the force efficiency and force guidance being restricted and unfavourable due to constructional conditions. The construction also leads to the risk of inadequate sterility and prevents re-use or reconstruction of the device. In a further known injection device (DE-AS 14 91 842) the needle bearing comprises a plunger with a deformable piston which can yield back into a cylindrical chamber so that mounting and construction are complicated, whilst the usability and efficiency are restricted by constructional and material requirements.

Other automatic injection devices not belonging to this species comprise a needle fixedly attached to a movable ampoule (DE-OS 24 31 347, DE-AS 19 34 117, DE-PS 24 36 000), a cap of an injection cannula being more particularly mounted on a needle holder (DE-OS 33 42 407).

In contrast thereto, the present invention is based on the task to provide an automatic injection device, which ensures a high speed ejection of the injection needle, whilst providing a uniform and clearly defined injection substance release, the arrangement and construction of the needle bearing being intended render usable, in an optimum manner, or to improve the possibilities of use and application, the construction and characteristics of the needle, cartridge, drive or pressure device, release mechanism and safety device, and, at the same time, the complete device having a long storability as well as a sterility ensuring type of construction of a particularly high mechanical efficiency, being provided to become operationally reliable, lightweight, robust, compact, of small construction, as well as simple, fast and without risk to handle and to become, owing to the possibility of a cartridge replacement and of the repeated use of device parts, reusable. A further object of the invention is to provide a compact cartridge or ampoule capable of being handled as such for an injection device, which shall be effortlessly insertable into an injection device as an independent component and which shall open up the random usability of an injection device for a multitude of injection substances, particularly also the administration of separate and, therefore, also injection substances not liquifiable per se and chemically reacting with one another on administration, a construction being aimed at which is simple and fail-safe as well and meets medical requirements by a high degree, so that, the ampoule or cartridge is particularly suitable for use in automatic injection devices.

The problem is solved with respect to an injection device and to a cartridge or ampoule insertable therein of the types described in the introduction, in that the needle body, over part of its extension, is designed as a needle bearing guided in a sliding fit on the inner wall of the cartridge. In the case of an ampoule or cartridge of the type described in the introduction, for the administration of separated injection substances, a receptacle such as a capsule forming a gas or dead volume is arranged within the ampoule, the receptacle having a receptacle wall resistant to the injection substance surrounding the receptacle, which receptacle wall is, in particular, not soluble in the injection substance and can easily be destroyed on initiating the lifting movement.

In the case of the integrated needle bearing formed by the needle body, it is, in particular, important that the needle or cannula is independently movable and guided in substantially friction-free manner with a type of floating effect in the injection substance. Thus, the needle can be advanced very rapidly in a substantially delay-free manner, and a high discharge capacity can be obtained. The needle bearing according to the invention is in itself sufficient to guide and position the needle, so that there is no need for further needle bearings, particularly in the ampoule discharge region. During operation the needle is also protected against damage or destruction and its movement and alignment are substantially free from the influences of the mounting of the lifting element or its movement behaviour. This means that the needle bearing is mechanically decoupled with respect to the lifting element or to a pressure device such that the transmission of force to the needle takes place without any disadvantageous effect on its alignment and whilst preventing damage thereto. This leads to a particularly simple, compact, robust, efficient, operationally reliable and easily handable ampoule and to an instrument with corresponding advantages, whose components are not impaired by the needle bearing as regards sterility as well as operation and re-usability, but can be provided with optimum adaptation and matching thereto.

If a precisely central ejection of the needle is desired, although unnecessary for automatic injection, a spacer disk supporting the needle alignment can be arranged within the ampoule, and preferably in the needle ejection region, which disk does not impair the substantially frictionless mobility of the needle obtained in accordance with the invention.

An embodiment of the needle bearing, according to the invention, consists in that it is constructed as a lifting element or a drive-side sealing element, it being integrated into a lifting plunger or being provided with a preferably thin-walled surface serving the needle advance and, in particular, being chargeable with the force of a fluid. Thus, the ampoule is made particularly small and the needle bearing can serve to the precise guidance and alignment of the lifting plunger or can itself act as the lifting element, the sliding fit, in part, forming the drive-side sealing of the ampoule.

It is particularly expedient for the needle bearing, in the case of a cylindrical cartridge or ampoule, to comprise at least one cannula winding establishing the sliding fit and, in particular, a terminal winding engages on a lifting element constructed as a lifting plunger. Such a winding cannula ensures a moment-free self-mounting of the needle, the sliding surface and, therefore, also the friction surface on the ampoule inner wall is minimized. A single winding leads to a particularly short cannula or needle. In accordance with the desired residual displacement volume, two or more windings can be shaped in closely juxtaposed or spaced manner. Particularly in the case of mass production, a particularly dimensionally accurate alignment of the needle point perpendicularly to the winding body is ensured with respect to a central passage through the ampoule seal.

Due to the design of the needle bearing as a cannula winding the needle may as well be aligned in a particularly simple manner at an angle of approximately 7°–15° with respect to the axis of the ampoule (cartridge or phial) or of the winding. The amount of the adjusted angle deviation from the axis is provided in accordance with the anatomical circumstances and facts. It is e.g. advantageous to choose a relatively large deviation for self-injections in the posterior region. The engagement of the terminal winding on the lifting plunger effects a delay-free, i.e. rapid force transfer possible under high force. An arrangement of the cannula inlet opening on the plunger-side winding end ensures an optimum fluid entry into and fluid passage through the cannula.

An injection substance quantity as well as a desired administration or application depth for the needle are expediently provided by the number of cannula windings and matched thereto with a compressible gas or dead volume i.e. in particular with a gas or air cushion leading to a defined delay of injection substance discharge.

According to a further development of the invention, it is provided that the needle is located in a front, separate ampoule space forming a dead volume and filled with a gas or gaseous mixture and to which on the drive side is connected a rear ampoule space containing the injection substance, separated by a sealing lifting element and formed between the latter and a lifting plunger; and the lifting element can be pierced during actuation by a formation in or on the needle and/or the needle bearing, said formation including the cannula inlet opening. Thus, there is obtained a cannula mounted in a dry manner in an air or gas space and which is therefore kept sterile. The dead volume, which is compressible to a higher degree with respect to the injection substance, additionally leads to a very short, defined delay of the discharge of the injection substance from the driven needle, i.e. the needle point exits from the ampoule prior to the ejection of injection substance, the delay being determined by the size of the dead volume and/or the distance of the open needle end to the lifting element. The gas or dead space located in defined manner in the front ampoule part ensures a delay independent of the alignment of the ampoule during injection. Freedom from blocking of the cannula opening is, in particular, ensured by a sufficient opening cross-section and/or an opening remote from the needle impact zone. The formation in or on the needle forming the needle end can be provided with a grinding and/or made pointed to facilitate penetration of the lifting element.

For a cartridge or ampoule for loading an injection device, or for an ampoule with a needle bearing according to the invention and/or the automatic injection device of the aforementioned type, the invention proposes that within the ampoule, in particular, between the needle bearing and the lifting element there is provided a gas- or dead-volume-forming receptacle, such as a capsule with a receptacle wall resistant to, in particular, not soluble by the injection substance, which receptacle can be destroyed easily by initiating the lifting movement. This leads to a dead volume arranged in the ampoule in a constantly defined manner and which is chemically and mechanically limited with respect to the injection substance without the aid of a lifting or plunger element and is only released in the case of a given pressure destruction. For the planned destruction of the receptacle and, at the start of injection, in order to permit the injection substance present in the region of the destroyed container to flow substantially into the cannula inlet opening, optionally in a delayed manner as a result of its immediate entry into a gas-dead-volume space, it is, in particular, provided that the needle and/or needle bearing has a formation therein or thereon engageable with the receptacle wall and leading to the destruction of the dead volume receptacle upon pressure application, which formation has, in particular, a pointed cannula end directed onto the receptacle wall, in particular, arranged adjacent thereto, the cannula inlet opening, for the purpose of flowing-in of the injection substance occurring upon destruction of the receptacle, being provided, in particular, free of obstruction by jamming, on the formation, especially with an adequately large inlet cross-section and/or remote from the receptacle wall. It is particularly expedient for the receptacle to contain at least one substance which, together with the ampoule contents engaging on the undestroyed receptacle, produces an injection substance to be administered. Thus, it is achieved that the solid, liquid and/or gas in the capsule are held separated from the injection substance, namely a solvent or a liquid injection medium engaging thereon, and kept ready and that, when the capsule is destroyed in the defined manner there is a mixing of liquids or a dissolving of solid and/or gas, so that a resultant injection substance flowing into the cannula opening is produced.

The self-mounting of the needle permits, in a particularly expedient manner, the ampoule to be designed as a receptacle of glass or similar material chemically resistant to the injection substance. As a result of the inventive needle bearing type according to the invention, the ampoule wall is free from unfavourable forces, so that glass can be used advantageously as the material not attacked, e.g. by an atropine sulphate solution.

With a view to a particularly compact construction, a replacement of an ampoule and/or substantially unlimited stability for a large number of injection substances, a particularly advantageous possibility consists in the cartridge or ampoule seal of the glass ampoule being designed as a silicone plate with a beaded tin plate rim, the needle being provided to lie completely in the interior of the ampoule and the plate to be penetrated by the needle. In place of silicone for the plate or tin plate for the beaded edge, it is possible to use other materials, particularly hardened plastics, which are inert with respect to injection substances and which satisfy mechanical and constructional requirements.

A cannula outlet opening provided with an outlet grinding favours, particularly, a rapid penetration of tissue parts having pain receptors and safeguards minimizing of trauma due to high cutting action. Moreover, a defined fluid release to be obtained according to the invention, particularly at low injection solution quantity, effects limited tissue pressure conditions.

In order to make interfaces coming into contact with injection fluids, such as the plate seal, the needle and a lifting element inert, the sealing plate consists of silicone or a plastic suitable in accordance with the injection substance, the cannula consists of a V2A or V4A steel bringing about a very good sliding action between the ampoule inner wall and needle bearing, and the cartridge or ampoule plunger consists of chlorinated or chlorobutyl caoutchouc or a plastic material depending on the injection substance.

Particularly for a simple changeover and for an easy replacement of the ampoule presenting these possibilities and having an integrated needle bearing, an embodiment of the automatic device according to the invention has, as its casing, a jacket casing and a closure cap laterally closing the casing in the region of the ampoule seal and mounting the cartridge or ampoule. It is particularly appropriate to design the closure cap as a spring catch arrestable by means of groove and tongue means and insertable into the jacket casing.

In the case of an injection device with a pressure device, which comprises a helical compression spring, a spring sleeve and a tappet or piston driving the lifting element as a result of spring pressure, a particularly advantageous embodiment of the device, made possible through the needle bearing according to the invention and the thus resulting construction of the ampoule, consists in that the spring is arranged and kept tensioned between a jacket casing and the spring sleeve, the spring sleeve is mounted displaceably on the jacket casing and is operatively connected to the piston and the cartridge or ampoule guiding and mounting the needle body in sliding fit directly on the inner wall thereof is so arranged that it extends into the arrangement area of the tensioned spring, in particular enveloping the ampoule, i.e. to this extent being directly above it. This arrangement leads to a particularly robust, functionally reliable, small injection device ensuring a high spring or driving force and therefore being efficient. Thereby, in particular, it is significant that only the piston is driven into the cartridge or ampoule, whilst the spring is separately mounted outside the cartridge between the jacket casing and spring sleeve, even in the case of untensioning thereof, i.e. comes into action outside the ampoule. The spring sleeve driving the piston ensures a particularly stabilized force action, i.e. a trouble-free, precisely aligned, linear piston drive. The force action and transmission, as well as the spacial arrangement within the device are particularly favourable, because the power source, i.e. the spring, is located in the vicinity of the ampoule lifting element in space-saving manner on the outside between the jacket casing and the ampoule even in the tensioned state. Thus, the ampoule is mounted in a very shockproof and, therefore, shatterproof manner. Thus, a particularly strong construction or dimensioning of the spring, i.e. a helical spring with a relatively large diameter and thick spring material whilst being tensionable to the smallest space is possible, but the particularly small construction of the overall device is not impaired. The free, independent ampoule needle bearing ensures such a compressed construction safeguarding a high driving force. This is, in particular, achieved in that the jacket casing is designed as a cylindrical, stepped sleeve with a front portion substantially surrounding the ampoule and a rear portion following thereafter via a shoulder and having a diameter smaller by the shoulder as compared with the front casing portion, the spring sleeve is mounted in the rear casing portion and also on the cylindrically designed ampoule in a movable manner and in the tensioned state of the pressure device, overlaps the same substantially along the extension of the tensioned helical compression spring, the spring being kept tensioned between the shoulder and an annular projection arranged at the overlapping end of the spring sleeve. When the device is in the tensioned state, this structure permits that the tappet of the piston is arranged to lie upstream of the inner end of the ampoule and outside the latter and that a tappet-side ampoule lifting element, particularly a lifting plunger terminates substantially with said end, a second lifting element enclosing a compressible space with the tappet-side lifting element, when necessary, being provided on the needle side, and that the piston is mounted at its rear end on the spring sleeve and is consequently drivable in the direction of the needle. It can be seen that the device is advantageously constructed with a spatially outwardly closed ampoule, the force being transferable to the needle-side lifting element via a suitable compressible space. When the device is in the tensioned state, it is also possible for the piston to enter the ampoule and pass through the helical spring, thereby engaging with its tappet on the plunger mounted at its other, rear end on the spring sleeve so that it is consequently drivable in the direction of the needle. The rear, tapered casing portion forms a space-saving, movement-stabilizing sleeve friction bearing for the spring sleeve, little space being required for the helical compression spring and the latter being located in a space-saving and space-utilizing manner between the casing jacket and ampoule and parallel to the latter, its operation not having a disadvantageous effect through the external arrangement thereof on the spring sleeve, so that, in particular, it is possible to use a per se fragile glass ampoule made possible through the needle bearing type according to the invention.

The needle bearing or ampoule design according to the invention enable a further development of the invention with a view to a particularly compact as well as sterility-ensuring construction of the device and/or particularly with respect to re-usability of device parts, which development resides in that in a known per se manner the release mechanism comprises a release sleeve which is axially displaceably arranged on a jacket casing and a release element movable therewith, as well as a spring element connected to the pressure device, arrested on the jacket casing and thereby keeping the pressure device in the tensioned state, the spring element being releasable from its spring seat when the release element strikes against it, and consequently the pressure device being releasable. Thus, the aforementioned subdivision of the jacket casing into a front and a rear portion enables, for the further improvement of the handy and practicable use of the self-injection syringe, that the release sleeve be small, easily operable and displaceably mounted on the rear, offset casing portion, only, in sliding fit in the direction of the shoulder.

In order to avoid an undesired release of the syringe, the instrument according to the invention can be equipped with a known per se safety device for a particularly reliable and effective operation, which safety device comprises a safety element with an engagement element engaging on the piston and keeping the same locked against the force of the spring. With regard to easy fitting possibilities and taking account of re-use, it is particularly appropriate for the safety element designed as a safety button to be mounted on a beaded rim frontally designed on the release sleeve and simultaneously forming the release element, and for the engagement element designed as a button pin or plug to engage in the rear end of the piston, which end is designed as the release spring element.

The individual parts of the device according to the invention as well as the latter itself can be inexpensively mass-produced. The combination of the parts leads to a particularly safely functioning, short device, ensuring the sterility necessary for injection. Inexpensive plastic casing parts can be made impermeable to light, so that even when using advantageous glass ampoules, light protection and therefore long-term storage are ensured. A helical compression spring is expediently constructed as a galvanized steel spring, which can, in particular, have a high spring pressure, without impairing the operational or functional reliability of the components and, in particular, of the ampoule. The glass ampoule embodiment leads to an only weak magnetic ampoule or device, in other words it is not unfavourably influenced in this respect from the ambience. The advantages attainable according to the invention are, in particular, that an automatic syringe and a cartridge or ampoule are obtained which, in the case of a construction ensuring sterility and high storage stability, are particularly handy, practical, operationally reliable and efficient, the ampoule enabling defined arrangements of gas or dead volumes, as well as the use of substantially all possibly relevant injection substances and, in particular, such substances which are separated, to be mixed or to be dissolved. Unskilled persons are given the possibility of an almost painless administration of an either subcutaneous or intramuscular self-injection. There is a possibility of a simple changeover and replacement of injection ampoules, together with the re-use of device parts. The needle/ampoule design according to the invention or the material structure attainable therewith for an ampoule, as well as the simple and reliable manner of construction and of operation resulting from the pressure device, release mechanism and safety device enable an almost unlimited life for a large number of injection substances, as well as a particularly safe operation meeting the particular requirements of medical application, the cannula passing out very rapidly so as to ensure freedom from pain and, depending on the positioning of an injector, it can optionally pierce clothing and a few millimetres of skin surface, without any injection fluid emerging when a dead volume is provided, but this is followed by a very rapid and deliberate fluid ejection.

BRIEF DESCRIPTION OF THE DRAWINGS

Further utilities, developments and embodiments of the invention can be gathered from the following description of the drawings.

FIGS. 2 to 4 are views of injection needles in accordance with the invention;

DESCRIPTION OF THE PREFERRED EMBODIMENTS

Figure 1:
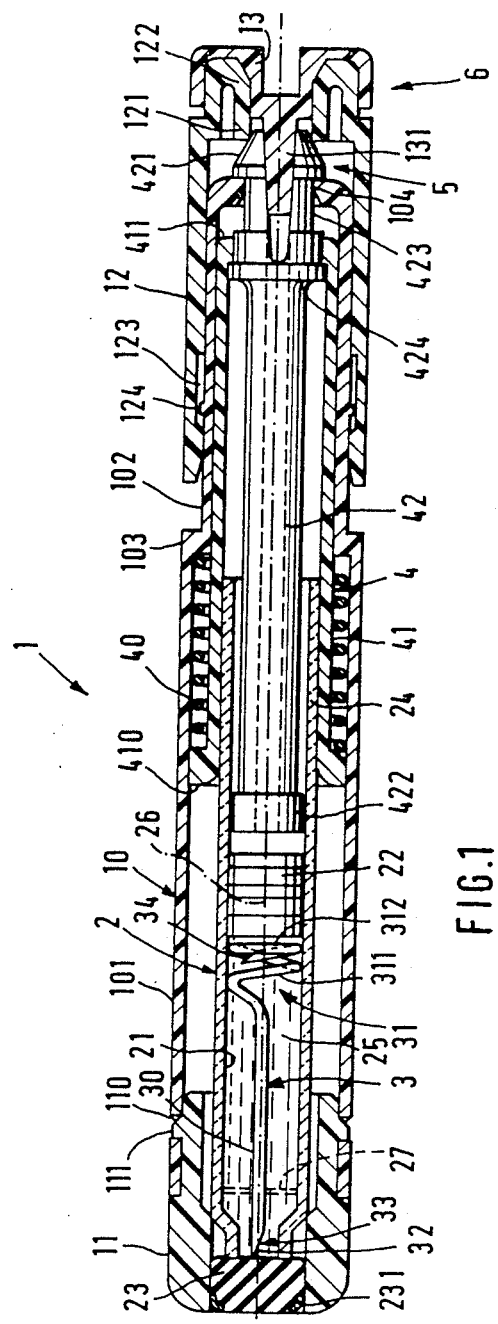
FIG. 1 is a side section view of an injection device in accordance with the invention with an ampoule mounted therein.

According to FIG. 1, an automatic injection device 1, which is in its tensioned state, comprises a one-piece, cylindrical jacket casing 10 with a front casing portion 101 and a smaller diameter rear casing portion 102 stepped with respect to the former by means of a shoulder 103. The front end of the injection device 1 is closed by a closure cap 11. An ampoule 2 in accordance with the invention is inserted in the casing portion 101 and is arrested with an unlockable snap catch having groove and tongue means 110/111. On the rear casing portion 102 there is provided, in sliding fit, a release sleeve 12 terminally closed with a safety button 13 as a safety element and which is held with a recess 123 in the sleeve and with an all-round thickened casing portion 124 on the rear casing portion 102. The latter mounts internally in sliding fit a cylindrical spring sleeve 41, which in turn mounts the ampoule 2 in sliding fit and can move over and beyond the same.

The ampoule or cartridge 2 in accordance with the invention as shown in FIG. 1 is designed as a cylindrical glass receptacle, which is sealed to the outside on the front side of the ampoule with a silicone plate 23 comprising a tin plate beaded rim 231. An injection fluid 25 is contained in the ampoule and preferably includes a solution of atropine sulphate, acid for pH-value setting, e.g. hydrochloric acid, a suitable salt for isotonization, e.g. sodium chloride and water for injection purposes. The injection fluid is between seal 23 and a liquid-sealing lifting plunger 22 lifting which is used as the element. Glass as the material for ampoule 2 ensures, over a long period, that the injection solution is maintained sterile and pyrogen-free, with suitable tonicity. Further, the desired pH-value can be maintained, whilst ensuring freedom from impurities according to standard purity criteria. Due to low thermal conductivity of the glass receptacle 2, heat transfer to the injection fluid, which can occur in the case of conventional metal ampoules, is avoided, so that the fluid is protected against decomposition by high temperatures and to this extent is kept stable.

In the case of the injection device according to FIG. 1, the lifting plunger 22, slidable in the ampoule 2, is located in the area in front of the inner end 410 of the spring sleeve 41. The rear end region 24 of ampoule 2 extends into the spring sleeve 41 up to the area of the casing shoulder 103. Outwardly, plunger 22 engages a tappet 422 of a piston 42, which, by means of an all-round bead 424 on the rear end 411 of the spring sleeve 41, is movable in the direction of the lifting plunger 22, the latter being advanceably mounted in the ampoule 2.

There is provided a hypodermic or injection needle 3 positioned completely within the ampoule 2, i.e. located in the fluid 25 between the seal 23 and the lifting plunger 22. It is designed as a winding cannula with two terminal cannula windings 311, 312, which, as winding bodies, form a needle bearing 31, in that the outer faces of the windings directly establish a sliding fit on the ampoule inner wall 21. The outer winding 312 forms a substantially planar abutment for the lifting plunger 22, so that the winding body can be driven forwardly linearly in the direction of its axis or the central axis of the ampoule 2 by means of the lifting plunger 22. With respect to a particularly small construction, and for establishing a bearing for a lifting plunger, it is appropriate to embed the winding body at least partly in the lifting plunger, whilst leaving free the winding's sliding faces. The winding 311 passes into an elongated cannula-needle body 30, which is aligned precisely in the ampoule central axis 26. To assist a precisely central alignment and guidance, it is possible to provide a spacer element not impairing a floating mounting of the needle and the free mobility thereof, in particular a spacer disk 27, indicated in broken line form, in the front area of the ampoule. The cannula is open at the end of the winding 312 by means of a cannula inlet opening 34 located on the lifting plunger 22 in the area of the abutment of the needle bearing 31. The needle point has a cannula outlet opening 33 provided with a grinding, which, during the ejection or drive of the needle 3, pierces the seal 23 in the axial direction 26. Immediately following the piercing, the fluid 25 is ejected through the cannula 30, 31 provided with the windings 311, 312.

Figure 4:
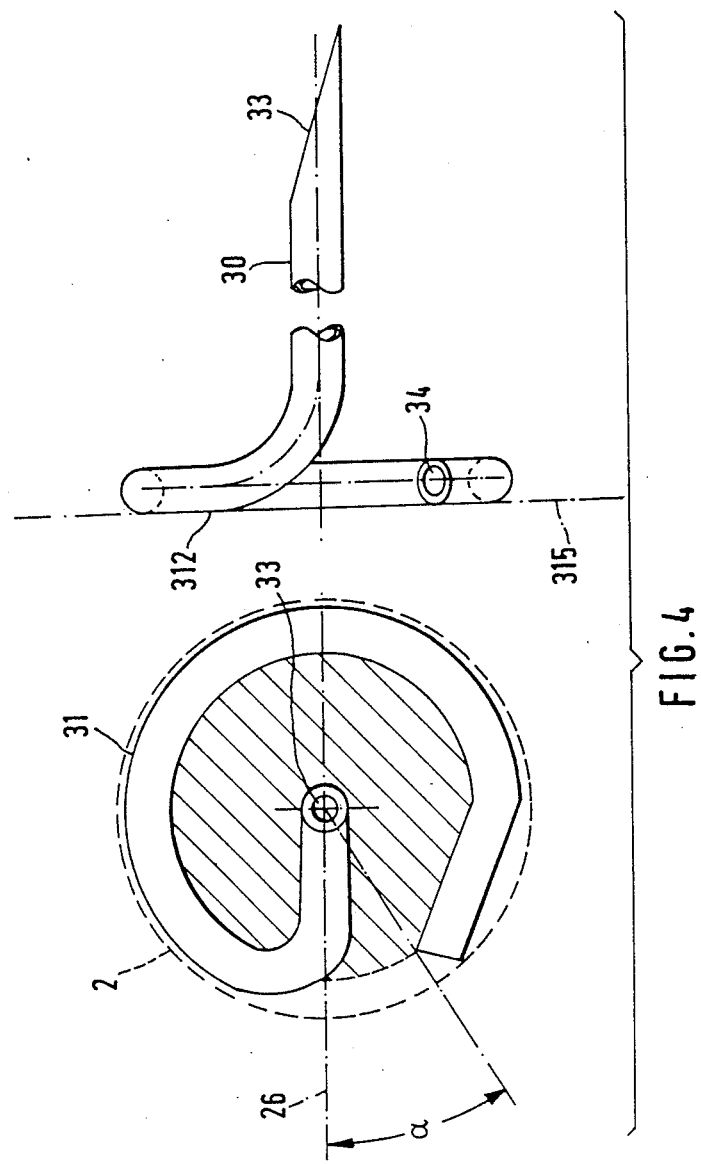

In FIG. 2 a front and a longitudinal view of the hypodermic needle 3 inserted in the ampoule according to FIG. 1 are represented. By means of the needle bearing 31, i.e. by the needle body substantially having two windings 311 and 312, bearing and sliding surfaces for the ampoule inner wall 21 are formed in the axial direction and transversely thereto on the circumference of the winding body, as can be seen at 313 and 314. The inlet opening 34 is positioned in protected manner within the winding body 31. The needle bearing in accordance with the invention can as well be provided with a winding body 31, essentially comprising one turn 312, only, as shown in FIG. 3. As shown in FIG. 4, a further embodiment for a needle 3 consists in that a terminal winding 312 is not closed completely, in that an aperture angle of, for example, 30° remains. An exact needle alignment and guidance is ensured with such a reduced winding construction, as well, because the needle body or needle shaft 30, in particular, floats in an injection fluid and is kept centred thereby. The described termina windings 312 are terminated with a winding surface 315 perpendicularly to the needle axis 26 at the end. With a view to obtaining a particularly short ampoule, it is particularly possible to mount or attach a thin-walled, closed surface element on a terminal turn 312 as is indicated by the hatched area in FIG. 4. Thus, the needle bearing is itself designed as a lifting element or a drive-side sealing element, so that there is no need for a separate ampoule plunger.

In FIG. 1, a pressure device 4 of the automatic injection device 1 comprises a spring sleeve 41, the piston 42 and a helical compression spring 40. The latter is kept tensioned in a space-saving manner externally on the spring sleeve 41 between the ring projection 410 and the shoulder 103 and thus is arranged between the casing portion 101 and the spring sleeve 41 in the rear end region 24 of the ampoule 2. This arrangement and space subdivision permit the use of a strongly dimensioned, i.e. a high spring energy-holding spring. The pressure device 4 or the spring 40 are tensioned by means of the rear end 423 of the piston 42, in that the end engages a mushroom-shaped spring element 421 against a terminal opening rim 104 of the casing portion 102.

A release mechanism 5 has a release sleeve 12 with a release element constructed as a rim 121 that is concentric to the mushroom head of the spring element 421, which rim compresses the mushroom head by striking against the same and consequently setting free the piston spring element 421 for the piston movement due to the force of the spring 40.

A safety device 6 has, as a safety element, the safety button 13 inserted in the rim 121 with a pin or plug 131, which engages in a groove of the mushroom head spring element 421, so that it is not compressible with the release element 121 and consequently the spring is reliably arrested in the tensioned state.

The casing components 10, 11, 12 and 13, as well as the ampoule seal 23 are designed as inexpensive, light-impermeable plastic elements. The glass ampoule 2 with the integrated sliding needle bearing 31 in combination with the snap cap 11 mounting the same, as well as with the arrangement and subdivision of the described components permits the re-use or new use of the device 1, with removability of the release sleeve 12 as well by unlocking locking device 123/124, in that the compact ampoule 2, which particularly meets medical requirements, can be substituted simply and the spring 40, designed as a galvanized steel spring, can be re-tensioned rapidly and easily, whereby the components 10, 40, 41 and 42 can consequently be used anew without replacement. The overall construction is short and has a limited weight, but this does not impair the robustness of the automatic injector.

The automatic injection device in accordance with the invention advantageously permits a liquid ejection quantity of approximately 0.7 g and a cannula exit length (between cannula tip and outer wall of the ampoule seal) of approximately 23 mm. The cannula exit time can, at a spring pressure of approximately 10.5 N/m$^2$, be approximately 0.5 s. The compact structure, in particular, permits an overall length of approximately 103 mm at a diameter of approximately 15 mm. Tests have shown that the ampoule with integrated winding cannula mounting ensures that, in the case of a dead volume provided at the cannula inlet opening during administration, the injection fluid immediately following the releasing of the device initially does not exit from the cannula, but is only ejected after penetrating a few millimetres of skin surface. Thus, the liquid discharge takes place in a defined and uniform manner and consequently establishes a favourable physiological depot in differing bleeding and tissue structures.

Figure 5A:
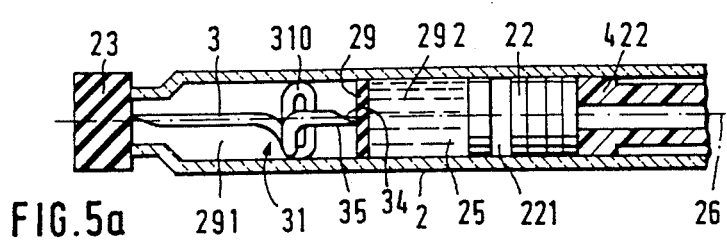
FIGS. 5a and 5b an ampoule in accordance with the invention with a sterile-manner mounted needle.
Figure 5B:
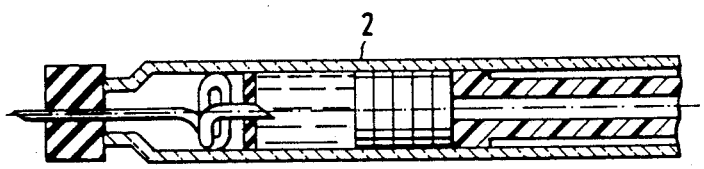

An ampoule, in accordance with the invention and to FIG. 5, comprises an air or gas space 291, in which is held, guided and mounted, in a sterile manner, a hypodermic needle 3 with a needle bearing 31 comprising one winding 310. To the space is connected, by means of a lifting-sealing element 29, an ampoule space 292 containing an injection solution 25 and which, on the drive side, is closed by a rubber plunger 22 as the lifting element. As can be taken from FIG. 5a, the plunger 22 comprises a dead volume or an air space 22 when the ampoule is in its non-operative state. Towards the side of the sealing element 29, the needle 3 has a spear-shaped formation 35 located in the ampoule axis 26 and comprising an inlet opening 34. Due to the easier compressibility of the gas space 291 as compared with the injection solution space 292, prior to its entry/passage of the tip 35 into or through the lifting-sealing element 29, the needle 3 is driven in liquid-free manner through the ampoule seal 23 over a given length and only then, as shown in FIG. 5, there occurs an inflow of liquid into the inlet opening 34 through the cannula. Together with the passage strength of the lifting-sealing element 29, the formation 35, dependent on the degrees of compression and/or volume in the two spaces 291, 292, determines the thus defined delayed liquid discharge.

Figure 6A:
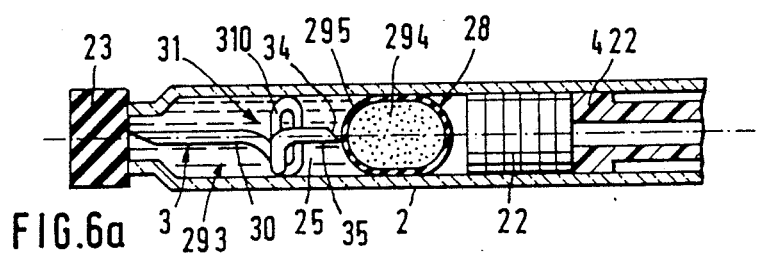
FIGS. 6a and 6b are section views of an ampoule in accordance with the invention with a capsule and floating needle.
Figure 6B:
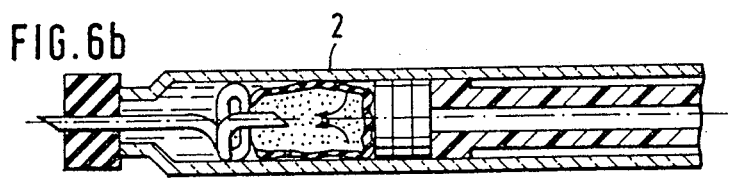

A cannula, in accordance with the invention and to FIG. 6, comprises a capsule 28 arranged between the injection substance space 293 and lifting plunger 22 and which has a capsule wall 295 chemically resistant to injection fluid 25. Due to the charging with pressure, the capsule 294 disintegrates (FIG. 6b), this destruction being initiated by a spear-shaped formation 35 having a cannula inlet opening 34. The capsule 294 is at least partly filled with solid, liquid and/or gas 294, two previously separate fluids being mixed or a solid and/or a gas being dissolved in liquid during or after capsule destruction, so that a resultant injection substance is obtained, which flows into the inlet opening 34 in a concentration forming in the capsule destruction area and is ejected with the complete ejection of the needle 3. It is, therefore, made possible to inject injection substances or injection components which have been kept separately, the direct arrangement of the formation 35 or the inlet opening 34 on receptacle wall 295, as shown in FIG. 6b, making it possible to ensure a delayed injection substance outlet due to the gas present in the capsule. The cannula winding bearing 31 in accordance with the invention, together with the needle body 30 floating in the injection solution 25 ensures an optimum mounting and guidance of the needle 3.

We claim:

1. An automatic injection device, comprising: a casing, an ampoule mounted in the casing and having an injection fluid, a lifting element, an injection needle having a needle point, an elongated needle body and a cannula wherein the needle is moved by engagement of the lifting element with an end portion of the needle opposite the needle point, a cannula inlet opening for the injection fluid disposed in the region of said one end, said ampoule having a seal adjacent the needle point such that the needle point pierces the seal and permits passage of the needle therethrough when the needle is moved by the lifting element, injection force means mounted on the casing for applying a force to the lifting element, release means for releasing the injection force means; and said needle having a needle bearing having at least one winding that is formed as a unitary part of the needle body and that has an outer sliding surface that is guided in a sliding fit on an inner wall of the ampoule.

2. An injection device according to claim 1, further including a spacer disk supporting the needle in alignment within the ampoule adjacent the needle point of the needle.

3. An injection device according to claim 1, wherein the needle bearing includes a lifting element integrated into a lifting plunger that is acted upon by said injection force means.

4. An injection device according to claim 1, wherein the ampoule is cylindrical and the needle bearing has two windings for establishing the sliding fit between the needle bearing and the inner wall of the ampoule.

5. An injection device according to claim 4, wherein said needle bearing includes a terminal winding as said end portion that engages the lifting element.

6. An injection device according to claim 4, further including a predetermined number of said windings, and said ampoule having a predetermined dead space volume such that a desired injection fluid quantity and administration depth for the needle are obtained.

7. An injection device according to claim 1, further including said ampoule having a front space forming a dead volume filled with a gas and the needle being positioned within said front space, and said ampoule further having a rear ampoule space containing the injection fluid and being separated by the sealing lifting element at one side of the contained injection fluid and a lifting plunger at the other side of said contained injection fluid; and said end portion of said needle having a piercing end and an adjacent cannula inlet opening for piercing said lifting seal element when said lifting plunger is moved by said force applying means such that said injection fluid is dispensed through said cannula inlet opening from said rear ampoule space.

8. An injection device according to claim 1, wherein the ampoule has a receptacle means disposed between the needle bearing and the lifting element for forming a dead volume filled with gas, said receptacle means having a receptacle wall resistant to the injection fluid and further being destroyed by movement of the lifting element.

9. An injection device according to claim 8, wherein said end portion of the needle is a piercing end positioned adjacent the receptacle wall, and said needle further having a cannula inlet opening adjacent said piercing end for receiving the flow of injection fluid into the cannula when said force applying means moves said lifting element to destroy said receptacle wall.

10. An injection device according to claim 8, wherein the receptacle has at least one substance contained therein that combines together with the injection fluid when the receptacle wall is destroyed to produce an injection fluid combination that is administered through the needle.

11. An injection device according to claim 1, wherein the ampoule is a receptacle that is chemically resistant to the injection fluid and is made from glass.

12. An injection device according to claim 1, wherein the ampoule seal has a silicone plate, and the needle is positioned to lie entirely within the interior of the ampoule such that the plate is pierced by the needle point when the lifting element is moved by said injection force means.

13. An injection device according to claim 1, wherein the injection needle has a cannula outlet opening adjacent the needle point, and further wherein the needle is made from one of V2A steel, V4A steel, Teflon, and hardened plastic.

14. An injection device according to claim 1, wherein the lifting element is made from one of chlorinated or chlorobutyl caoutchouc, silicone and hardened plastic that is inert with respect to the injection fluid.

15. An injection device according to claim 1, wherein the casing has a jacket casing and a closure cap for laterally closing the casing in the region of the ampoule seal, and further wherein said casing receives the ampoule.

16. An injection device according to claim 15, wherein the closure has a spring catch that is inserted into the jacket casing and is arrested by groove and tongue means for preventing movement of the closure with respect to the jacket casing.

17. An injection device according to claim 1, further including said injection force means having a helical compression spring surrounding a spring sleeve, a piston drivingly connected with said injection force means for driving the lifting element, the helical compression spring being positioned between the casing and the spring sleeve in a tensioned state, said spring sleeve being mounted for movement with respect to the casing and being drivingly connected to the piston, and the ampoule being received within the casing in alignment with the piston such that release of the tension in the helical compression spring moves the spring sleeve with respect to the casing and correspondingly drives the piston toward the lifting element for moving the lifting element.

18. An injection device according to claim 17, wherein the jacket casing has a cylindrical, stepped sleeve with a front end portion substantially surrounding the ampoule, a rear portion and a stepped portion between said front and rear portions, said stepped portion having a smaller diameter than the front portion to define a shoulder; the spring sleeve being mounted in the rear portion of the casing and extending into the front end portion; and the ampoule being received within the spring sleeve such that the spring is held in tension between the shoulder and an annular projection extending outwardly from the spring sleeve at a portion of the spring sleeve that receives the ampoule.

19. An injection device according to claim 17, wherein the piston is positioned in alignment with an inner portion of one end of the ampoule and said lifting plunger is positioned within said ampoule substantially at said one end; and a second lifting element enclosing an ampoule space having compressible air contained therein such that the piston is moved from an end opposite to the second lifting element and is driven in the direction of the needle.

20. An injection device according to claim 17, wherein the piston is positioned in alignment with an inner portion of one end of the ampoule, the piston having a tappet end portion that engages the lifting element and an opposite end portion that engages the spring sleeve for driving the tappet into engagement with the lifting element.

21. An injection device according to claim 1, wherein the release means has a release sleeve mounted for movement with respect to the casing in an axial direction and a release element facing a plug end of said spring sleeve such that an axial movement of said release element releases the spring sleeve from a first position relative to the casing wherein the helical compression spring is in a tensioned state so that said lifting element is moved by helical compression spring driver movement of the spring sleeve.

22. An injection device according to claim 18, wherein the release sleeve is mounted for relative sliding movement within the rear portion of the casing for movement in the direction of the shoulder.

23. An injection device according to claim 21, further including means for blocking the release of said release means including a safety device having a safety element that engages an end of the piston opposite to an end engaging the lifting element for preventing movement of the piston with respect to the casing.

24. An injection device according to claim 23, wherein said safety element is a safety button mounted on a bead rim and facing the release sleeve and engaging the release sleeve plug element for blocking the movement of said piston.

25. An injection device according to claim 1, wherein the needle bearing includes a lifting element integrated into a lifting plunger having a thin-walled surface that is acted upon by said injection force applying means.

26. A cartridge for an automatic hypodermic syringe containing an injection fluid, a lifting element and a hypodermic needle therein, comprising:
said needle having a needle point, an elongated needle body and a cannula wherein the needle is moved by engagement of an end portion of the needle opposite the needle point with the lifting element;
the cannula having an inlet opening for the injection fluid; a seal for sealing the ampoule at the end adjacent a point of the needle, said needle point penetrating the seal when the needle is moved by the lifting element; and
the needle having a needle bearing having at least one winding that is formed as a unitary part of the needle body and that has an outer sliding surface that is guided in a sliding fit on an inner wall of the cartridge.

27. A cartridge according to claim 26, further including a spacer disk supporting the needle in alignment within the cartridge at the needle point side of the cartridge.

28. A cartridge according to claim 26, wherein the needle bearing includes a lifting element integrated into a lifting plunger that is charged with the force of a fluid.

29. A cartridge according to claim 26, wherein the cartridge is cylindrical and the needle bearing has two windings for establishing the sliding fit between the needle bearing and the inner wall of the cartridge.

30. A cartridge according to claim 29, wherein said needle bearing includes a terminal winding as said end portion that engages the lifting element.

31. A cartridge according to claim 29, further including said needle bearing having a predetermined number of said windings, and said cartridge having a predetermined dead space volume filled with a compressible gas such that a desired injection fluid quantity and administration depth for the needle are obtained.

32. A cartridge according to claim 26, further including said cartridge having a front space forming a dead volume filled with a gas and the needle being positioned within said front space, and said cartridge further having a rear cartridge space containing the injection fluid and being separated by the sealing lifting element at one side of the contained injection fluid and a lifting plunger at the other side of said contained injection fluid; and said end portion of said needle having a piercing end and an adjacent cannula inlet opening for piercing said lifting seal element when said lifting plunger is moved such that said injection fluid is dispensed through said cannula inlet opening from said rear cartridge space.

33. A cartridge according to claim 26, wherein the cartridge has a receptacle means disposed between the needle bearing and the lifting element for forming a dead volume space filled with gas, said receptacle means having a receptacle wall resistant to the injection fluid and further being destroyed by movement of the lifting element.

34. A cartridge according to claim 33, wherein said end portion of the needle is a piercing end positioned adjacent the receptacle wall, and said needle further has a cannula inlet opening adjacent said piercing end for receiving the flow of injection fluid into the cannula when said receptacle wall is destroyed by movement of the lifting element.

35. A cartridge according to claim 33, wherein the receptacle has at least one substance contained therein that combines together with the injection fluid when the receptacle is destroyed to produce an injection fluid combination that is administered through the needle.

36. A cartridge according to claim 26, wherein said cartridge is a receptacle that is chemically resistant to the injection fluid and is made from glass.

37. A cartridge according to claim 26, wherein the cartridge seal has a silicone plate, and the needle is positioned to lie entirely within the interior of the cartridge such that the plate is pierced by the needle point when the lifting element is moved.

38. A cartridge according to claim 26, wherein the injection needle has a cannula outlet opening adjacent the needle point, and further wherein the needle is made from one of V2A steel, V4A steel, Teflon, and hardened plastic.

39. A cartridge according to claim 26, wherein the lifting element is made from one of chlorinated or chlorobutyl caoutchouc, silicone and hardened plastic that is inert with respect to the injection fluid.

40. A cartridge according to claim 26, wherein the needle bearing includes a lifting element having a thin-walled surface that is charged with the force of a fluid.

41. A cartridge for an automatic hypodermic syringe, comprising:
    a hypodermic needle having an elongated needle body and a cannula and being mounted in the cartridge;
    means for ejecting an injection fluid in the cartridge through the cannula of the hypodermic needle;
    said ejecting means including lifting movement means for lifting a plunger;
    a receptacle contained within the cartridge for forming a dead volume having a receptacle wall that is insoluble to the injection fluid and that contains at least one substance, and said wall being destroyed by said lifting means whereby the substance is combined with the injection fluid to produce an injection fluid combination that is administered through the needle.

42. A cartridge according to claim 41, wherein said hypodermic needle has a needle bearing having at least one winding that is formed as a unitary part of the needle body and that has an outer sliding surface that is guided in a sliding fit on an inner wall of the cartridge.

* * * * *